United States Patent [19]
Siegel et al.

[11] Patent Number: 5,721,434
[45] Date of Patent: Feb. 24, 1998

[54] DIGITAL DIAGNOSTIC SYSTEM FOR OPTICAL PAPER PATH SENSORS

[75] Inventors: Robert P. Siegel, Penfield; Fred F. Hubble, III, Rochester, both of N.Y.

[73] Assignee: Xerox Corporation, Stamford, Conn.

[21] Appl. No.: 733,852

[22] Filed: Oct. 18, 1996

[51] Int. Cl.$^6$ .................................................. G01N 21/86
[52] U.S. Cl. .......................... 250/559.1; 250/559.45; 358/504
[58] Field of Search ............................ 250/559.1, 559.01, 250/214.1, 214 R, 559.4, 559.45; 358/504, 406; 399/46, 50, 49, 74, 52; 356/445, 243

[56] References Cited

U.S. PATENT DOCUMENTS

| | | | |
|---|---|---|---|
| 3,970,393 | 7/1976 | Krygeris et al. | 250/559.1 |
| 5,075,543 | 12/1991 | Courtney | 250/223 |
| 5,139,339 | 8/1992 | Courtney | 356/446 |

Primary Examiner—Que Le
Attorney, Agent, or Firm—Ronald F. Chapuran

[57] ABSTRACT

A device for diagnosing the condition of copy substrate sensors including a transparent test document supposing a plurality of stripes of predetermined optical density The stripes are arranged in descending optical density about a stripe of maximum density and a transporter conveys the test document into communication with the optical path of each sensor. Circuitry responds to the stripes of predetermined optical density to provide a timing pulse of response of each sensor to the test document. The timing pulse is a. digital step pulse identifying the range of optical sensitivity each sensor and the step pulse represents a given set of stripes that provide a detector signal exceeding a threshold value.

22 Claims, 3 Drawing Sheets

DIGITAL DIAGNOSTIC SYSTEM FOR OPTICAL PAPER PATH SENSORS

This invention relates generally to an electrophotographic printing machine. More specifically, the invention concerns a diagnostic system to easily determine the condition of any number of paper path sensors using a simple run time test.

A major concern in reproduction machines has been reliable paper sensing over the product life, particularly with regard to high volume machines. Sensors are very sensitive to degradation over the life of the machine by such things as mechanical wear, dirt (paper fiber), and other debris within the copier environment. A difficulty with the prior art copy sheet sensors is not only the susceptibility to wear and tear and degradation over the life of the machine, but also the inability to determine the level of degradation. Despite the sophisticated electronic capabilities and impressive print quality and resolution, paper jams continue to frustrate operators. Therefore, the use of throughbeam or transmissive optical sensors is increasing due to the ability to provide noncontact copy sheet detection.

U.S. Pat. No. 5,075,543, for example, discloses a light detector disposed at the end of a light beam path, responsive to light projected along the light beam path providing an indication of the presence or absence of sheets of varying thicknesses in the light beam path. An optical fiber provides a portion of the light beam path for redirecting the light beam across the paper path, the light beam path being projected at an angle with respect to the paper path.

U.S. Pat. No. 5,139,339 discloses a sensor which can discriminate between paper and transparency as well detect the presence of either media. The sensor employs a light emitting diode and two photodetectors configured to measure both diffuse and specular reflectivity.

However, the failure modes of these types of sensors still contributes to jam rate. The primary failure modes are still contamination of the optical surfaces and degradation of the LED light source, with contamination being the more common. Both of these are manifested in essentially the same way, reduced sensitivity. A sensor which is contaminated (or with diminished light output) has a reduced range of contrasts to which it can respond. A dirty sensor may indicate the presence of paper when there is none or it may indicate the absence of paper when paper is present. Field diagnostics today primary look at jam rates and the contribution of the sensor is inferred as part of a fault tree generally after other causes have been eliminated.

Direct measurements of the sensors are performed in signature analysis systems where the input current to the LED is varied and the detector output monitored to assure that the sensitivity is in the correct range. However, this generally works well only in a factory setting. It has a couple of limitations, particularly with respect to field implementation. The first problem is that the monitoring function requires an analog read capability which is not generally in the machine. The second problem is that the ability to vary the LED current is not provided for in the machine, nor is there any practical way for the tech rep to do this. This problem will be compounded in the future as new, low cost sensors combine the 5V source to the LED with the source to the detector, so that it will no longer be possible to vary the input to the LED independent of the detector, and perform this test even in a factory setting.

It would be desirable, therefore, to be able to determine the condition of a sensor in a machine without the need for an analog read capability and without the need to vary LED current. It is an object, therefore, of the present invention, to provide a special test document and simple timing measurement to be able to determine the condition of a sensor in the normal operating environment.

Other advantages of the present invention will become apparent as the following description proceeds, and the features characterizing the invention will be pointed out with particularity in the claims annexed to and forming a part of this specification.

SUMMARY OF THE INVENTION

The invention is a device for diagnosing the condition of copy substrate sensors including a transparent test document supporting a plurality of stripes of predetermined optical density. The stripes are arranged in descending optical density about a stripe of maximum density and a transporter conveys the test document into communication with the optical path of each sensor. Circuitry responds to the stripes of predetermined optical density to provide a timing pulse of response of each sensor. The timing pulse is a digital step pulse identifying the range of optical sensitivity of each sensor. The step pulse represents a given set of stripes that provide a detector signal exceeding a threshold value. The test document and a test algorithm can be installed into the products control system, a tech rep laptop, or a manufacturing test system.

For a better understanding of the present invention, reference may be had to the accompanying drawings wherein the same reference numerals have been applied to like parts and wherein:

DESCRIPTION OF THE INVENTION

While the present invention will hereinafter be described in connection with a preferred embodiment thereof, it will be understood that it is not intended to limit the invention to that embodiment. On the contrary, it is intended to cover all alternatives, modifications and equivalents that may be included within the spirit and scope of the invention as defined by the appended claims.

Figure 1:
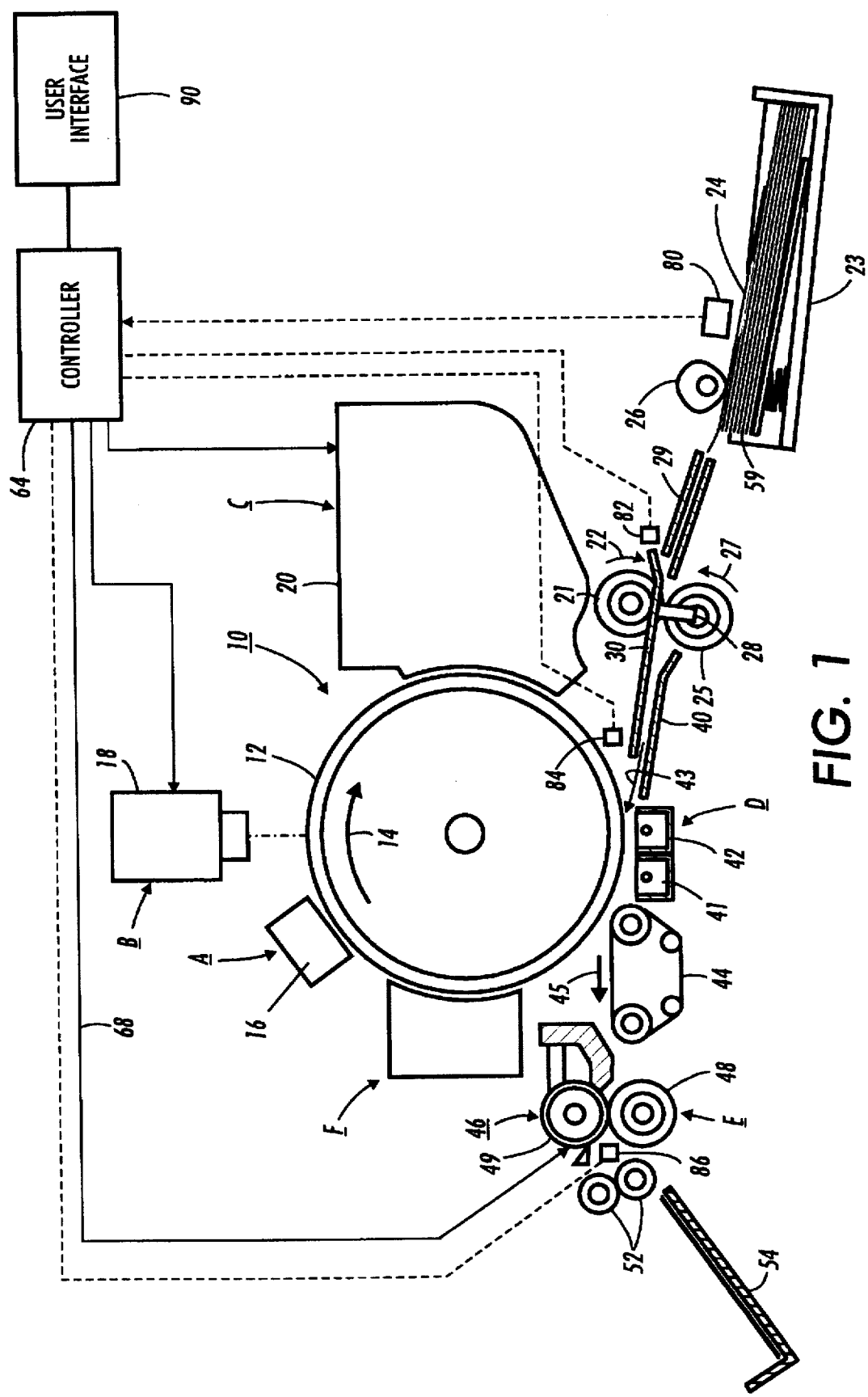
FIG. 1 is an schematic elevational view of a printing machine in which the present invention can be used.

With reference to FIG. 1, drum 10 has a photoconductive surface 12 entrained about and secured to the exterior surface of a conductive substrate. By way of example, photoconductive surface 12 may be made from selenium and the conductive substrate may be made from aluminum. Drum 10 is rotated in the direction of arrow 14 through the various processing stations..

Drum 10 initially rotates a portion of photoconductive surface 12 through charging station A. Charging station employs a conventional corona generating device, generally indicated by reference numeral 16, to charge photoconductive surface 12 to a relatively high and substantially uniform potential. Thereafter, drum 10 rotates the charged portion of photoconductive surface 12 to exposure station B. Exposure station B includes an exposure mechanism, indicated generally by reference numeral 18, having a stationary, transparent platen, such as a glass plate for supporting an original document thereon. Lamps illuminate the original document. Scanning of the original document is achieved by oscillating a mirror in a timed relationship with the movement of drum 10. Alternatively, the lamps and lens may be translated across the original document to create incremental light images. These incremental light images are projected through an aperture slot onto the charged portion of photoconductive surface 12. Illumination of the charged portion of photoconductive surface 12 records an electrostatic latent image corresponding to the information areas contained within the original document.

Electronic imaging of page image information could also be used, if desired. One skilled in the art will appreciate that a Raster Input Scanner (RIS) and a Raster Output Scanner (ROS) may be used instead of the light lens system heretofore described. The RIS contains document illumination lamps, optics, a mechanical scanning mechanism, and photosensitive elements, such as Charge-Coupled Device (CCD) arrays. The RIS captures the entire image from the original document and converts it to a series of raster scan lines. The raster scan lines are sent out from the RIS and function as the input to the ROS. The ROS performs the function of creating the output copy of the image and lays out the image in a series of pixels per inch. These lines illuminate the charged portion of the photoconductive surface 12 to selectively discharge the charge thereon. An exemplary ROS has lasers, rotating polygon mirror blocks, solid state modulator bars, and mirrors. Still another type of exposure system would utilize a ROS that is controlled by the output from an Electronic Subsystem (ESS). As the control electronics for the ROS, the ESS (which may be a self contained and dedicated minicomputer) prepares and manages the image data flow between a host computer and the ROS.

Drum 10 rotates the electrostatic latent image recorded on photoconductive surface 12 to development station C. Development station C includes a developer unit, indicated generally by the reference numeral 20, having a housing with a supply of developer mix contained therein. The developer mix comprises carrier granules with toner particles adhering triboelectrically thereto. Preferably, the carrier granules are formed from a magnetic material with the toner particles made from a heat seatable plastic. Developer unit 20 is preferably a magnetic brush development system. A system of this type moves the developer mix through a directional flux field to form a brush thereof. The electrostatic latent image recorded on photoconductive surface 12 is developed by bringing the brush of developer mix into contact therewith. In this manner, the toner particles are attracted from the carrier granules to the latent image forming a toner powder image on photoconductive surface 12. One skilled in the art will appreciate that a liquid developer material may be used instead of a dry developer mix.

With continued reference to FIG. 1, a single copy substrate 24 is advanced from tray 23. Sheet feeding apparatus 26 rotates so as to move copy substrate 24 from the uppermost position of a stack 59 and onto transport 29. Transport 29 forwards substrate 24 to registration roller 25 and idler roller 21. Registration roller 25 is driven by a motor (not shown) in the direction of arrow 27. Idler roll 21 rotates in the direction of arrow 22 as result of its contact with roller 25. As copy substrate 24 is advanced to rollers 25 and 21, it is positioned against registration fingers 28. Registration fingers 28 are actuated by conventional means in a timed relation with the image on photoconductive surface 12. Thus, copy substrate 24 is forwarded towards photoconductive surface 12 in synchronized registration with the image on photoconductive surface 12. Copy substrate 24 then advances, in a direction indicated by arrow 43, through a chute formed by guides 30 and 40 to transfer station D.

Transfer station D includes a corona generating device 42. Corona generating device 42 applies an electrostatic transfer charge to the underside of copy substrate 24 and electrostatically tacks copy substrate 24 against photoconductive surface 12. The electrostatic transfer charge attracts the toner image from photoconductive surface 12 to copy substrate 24.

After transfer, copy substrate 24 is transported on the photoconductive surface to corona generator 41. Corona generating device 41 serves to neutralize most of the transfer charge on copy substrate 24. It is not desirable to remove all of the transfer charge because that may reduce the electrostatic retention of the toner image to copy substrate 24. However, the amount of detack charge (preferably applied with an alternating current corona emission) is sufficient to allow copy substrate 24 to self strip from the photoconductive surface 12. Next, the copy substrate 24 moves onto transport 44. Transport 44 is an endless belt conveyor which advances the copy substrate 24, in the direction of arrow 45, to fusing station E. Fusing station E generally includes a heated fuser roller 48 and a backup roller 49 for permanently affixing the transferred toner image to copy substrate 24. After the fusing process is completed, the copy sheet is advanced by rollers 52 to a catch tray 54 for removal by an operator.

After the copy substrate 24 is separated from photoconductive surface 12, some residual toner particles remain adhered to photoconductive surface 12. These toner particles are removed at cleaning station F. Cleaning station F includes a corona generating device (not shown) adapted to neutralize the remaining electrostatic charge on photoconductive 12 and that of the residual toner particles. The neutralized toner particles are then cleaned from photoconductive surface 12 by a rotatable fibrous brush (not shown) in contact therewith. Subsequent to cleaning, a discharge lamp (not shown) floods photoconductive surface 12 with light to dissipate any residual electrostatic charge thereon before the next imaging cycle.

Throughout the machine, various copy sheet detection sensors are positioned, as illustrated by sensor 80 at sheet tray 23, sensor 82 at registration rollers 21, 25, sensor 84 at transfer station D, and sensor 86 at fuser rollers 48, 49. These sensors provide appropriate signals to controller 64 connected to user interface 90 on the presence or absence of copy sheets at the sensor locations.

Figure 2:
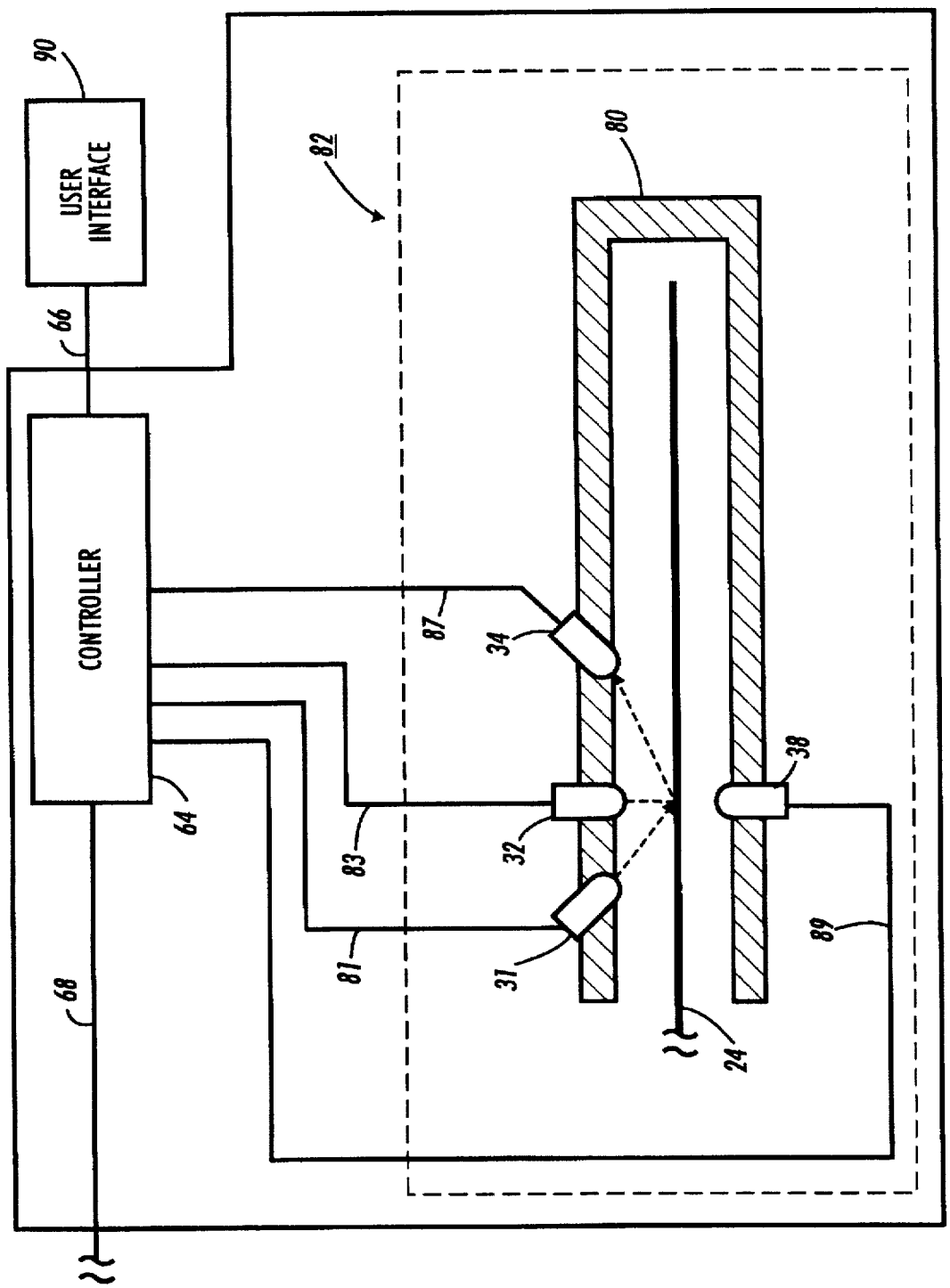
FIG. 2 is a schematic representation of an integrated multifunctional copy substrate sensor embodying the present invention.

FIG. 2 shows a composite arrangement for typical sheet detector sensors. In one scenario, a typical reflective sensor includes a suitable light source such as LED 31 linked to controller 64 by connector 81 and detector 34 responsive to light reflected from copy sheet 24 to convey signals to controller 64 via conductor 87. In another scenario, a typical transmissive sensor includes a light source such as LED 32 projecting light toward detector 38, the level of light to be received by detector 38 being dependent upon the absence or presence of a copy sheet between LED 32 and detector 38. LED 32 and detector 38 are interconnected to controller 64 over lines 83 and 89. Controller 64 controls the operation of the sensors and generally comprises a microcontroller of the type that is typically used for controlling machine operations in electrophotographic reproduction machines, facsimile machines, printers, and the like. Controller 64 typically has a CPU (Central Processing Unit), ROM (Read Only Memory), RAM (Random Access Memory), and I/O (Input/Output) interfaces for the light sources, detectors, and other xerographic components. Copy quality adjustments to xerographic components are made by controller 64 via various output lines such as 66 and 68.

In accordance with the present invention, there is provided, a means of determining the condition of a sensor, which does not require adjusting the LED input current, nor does it require an analog read capability to monitor the detector output. These functions are performed instead by a special document and a simple timing measurement.

The system consists of the special test document and a software algorithm which can be installed into the product's control system, a tech rep's laptop, or a manufacturing test system. The system uses the same digital timing information currently used on products and can determine the state of the sensors in a continuous sense without the use of an ND converter.

The special document is shown in the FIG. 3 below. The document is made of a transparent material with mechanical properties which are similar to paper. Imprinted on the document are a number of stripes of a known density. These are shown as A, B, C, & D in the FIG. 3. As we move from the edge to the center of the sheet in the direction of travel (from D to C to B to A) the stripe gets darker and more opaque. As the document passes through a transmissive sensor, the portion of the stripe which is seen by the sensor will be represented as a timing pulse (which is shown in the figure as a digital "high" level).

The duration of the "high" pulse tells us how much of the document is seen by each sensor and thus there can be determined within some range (as defined by the document construction) the current state of sensitivity for each sensor. This serves the same function as the former process wherein the current to the LED was varied in a prescribed manner and the resulting detector output read by some analog input means. In the example in FIG. 3, Sensor 1 switches high in response to stripes A, B & C, while Sensor 2 has a trip point which only responds to A & B. Neither sensor sees stripe D in this example. A very contaminated sensor which is already near the trip point, in the absence of paper, might trigger on D which would indicate a potential problem. As an alternative to the discrete stripes shown below, continuous resolution can be achieved with a gray scale sweep.

Figure 3:
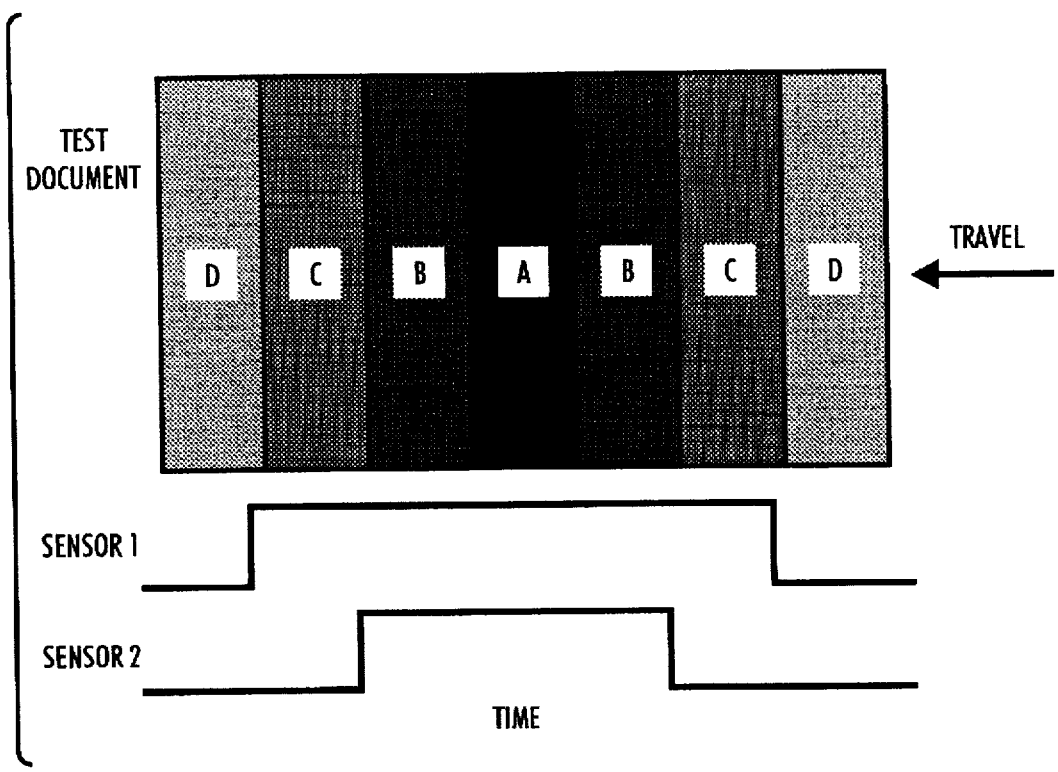
FIG. 3 illustrates a test document in accordance with the present invention.

In particular, the transparent test document, shown in FIG. 3, supports multiple stripes of predetermined optical density arranged in descending optical density about a stripe of maximum density. A transporter as illustrated in FIG. 1 conveys the test document into communication with the optical path of each sensor. Circuitry responsive to stripes of predetermined optical density provides a timing pulse of response of each sensor to the test document. The timing pulses are digital step pulses identifying the range of optical sensitivity of each sensor. As shown, the step pulse represents a given set of stripes providing a detector signal exceeding a threshold value.

It should also be noted that the width of the digital step pulse is a function of the speed of the test document. That is, for two given sensors responsive to the same set of density stripes, any variation in the width of the timing pulse is, in fact, a measurement of the actual speed of the document past the sensor. Timing marks a known distance apart can be added near the ends of the sheet as a feature to distinguish speed variations from density response variations. Thus, in accordance with another aspect of the present invention, the timing pulses represent copy sheet speed and can be used to monitor and adjust the speed of movement of copy sheets. In a preferred embodiment, this could be done by suitable responses of the controller 64 to selectively adjust copy sheet drives at each sensor. Suitable memory in controller 64 would record timing pulse readings in relation to each given sensor.

It should also be noted that there are various levels of sensor diagnosis contemplated within the scope of the present invention. That is, the degree of response or set of density stripes that a sensor recognizes would determine the condition of the sensor. For example, at a first level, a timing pulse signal indicating a response to only a minimal number of stripes could indicate that a sensor has deteriorated to a condition requiring immediate replacement or cleaning. At a second level, a timing pulse signal indicating a response to more than a minimal number of stripes, but less than a preferred number of stripes, could indicate that a sensor has deteriorated, but replacement or cleaning could be deferred to a future date. Additional levels of diagnosis based upon the sensor sensitivity to the test document could result in manual or automatic adjustment of sensor parameters, enabling continuing sensor operation without replacement. For example, logic circuitry could respond to sensor timing pulses to adjust power to the sensor or to change the threshold level of the sensor. It should also be noted that, while the preferred embodiment has been described using transmissive sensors and a test document of varying transmissivity, the technique is equally applicable to reflective sensors interrogated in a similar manner with a test document of varying reflectivity.

Figure 4:
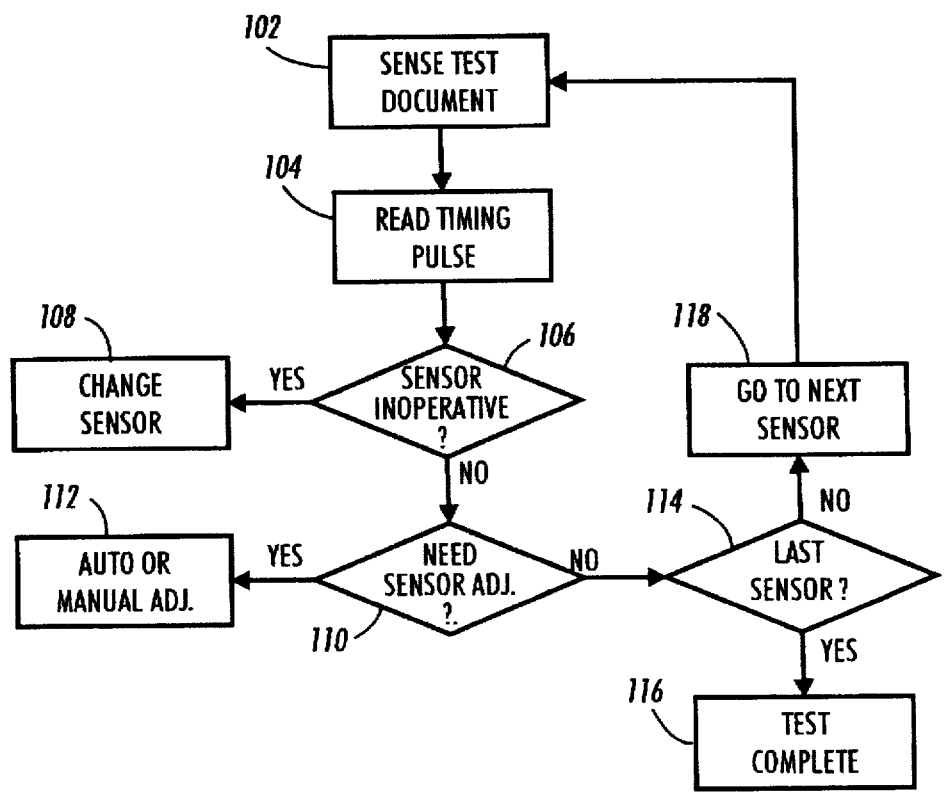
FIG. 4 is a flow chart illustrating the document test procedure in accordance with the present invention.

In accordance with the present invention, with reference to FIG. 4, block 102 illustrates the sensing of a test document. At block 104, the sensor scans the test document and responds to a given set of the test stripes of known density and produces a related timing pulse. A first level of response to the timing pulse is illustrated at decision block 106. In particular, based on the width of the timing pulse, that is, the number of test stripes that have been recognized or the degree of sensitivity of the sensor, a determination is whether or not the sensor is inoperative. If inoperative, block 108 represents the need to change the sensor. Note that the decision to change the sensor could be an immediate decision or based upon the degree of sensitivity of the sensor, could be a deferred decision.

If the sensor is operative and need not be changed, then a second level of adjustment is whether or not there is a need for a sensor adjustment as shown in decision block 110. If the sensor has deteriorated to a condition requiring some adjustment, as evidenced by the width of the timing pulse, then there is a sensor adjustment, either automatic or manual as shown in block 112. On the other hand, if the sensor is operative and in no need of adjustment, there is a determination as to whether or not in the sensor diagnostic procedure, all the sensors have been exposed to the test document for monitoring. If all the sensors have been tested and monitored, the test is complete as illustrated at block 116. If not, as shown in block 118 the diagnostic analysis continues to the next sensor in the test document path for sensing of the next test document as shown in block 102.

While the invention has been described in conjunction with a preferred embodiment thereof, it is evident that many alternatives, modifications, and variations may be apparent to those skilled in the art. Accordingly, it is intended to embrace all such alternatives, modifications, and variations which are within the spirit and broad scope of the appended claims.

We claim:

1. An apparatus for diagnosing the condition of copy substrate sensors, each sensor including a light source and a light detector in receiving relationship to the light source, the light source and light detector providing an optical path, comprising:

a test document including a plurality of sections of predetermined optical density, the sections being arranged in symmetrical order about a section of maximum density, a transporter for conveying the test document into communication with the optical path of each sensor, and circuitry responsive to the stripes of predetermined optical density to provide a timing pulse of response of each sensor to the test document, the timing pulse being a function of the range of optical sensitivity of each sensor.

2. An apparatus according to claim 1 wherein the sections are arranged in stripes of descending optical density about a stripe of maximum density.

3. An apparatus according to claim 1 wherein the timing pulse is a digital step pulse identifying the range of optical sensitivity each sensor.

4. An apparatus according to claim 3 wherein the width of the digital step pulse is capable of indicating the speed of the test document.

5. An apparatus according to claim 1 wherein the test document is a transparency supporting the plurality of sections of predetermined optical density.

6. An apparatus according to claim 3 wherein the step pulse represents a given set of stripes providing a detector signal exceeding a threshold value.

7. An apparatus according to claim 1 including a logic device responsive to the timing pulse of a given sensor for automatically adjusting said sensor to detect a predetermined number of sections.

8. An apparatus according to claim 7 wherein the logic device adjusts the power to the sensor.

9. An apparatus according to claim 7 wherein the logic device adjusts the threshold value.

10. An apparatus for diagnosing the condition of copy substrate sensors, each sensor including a light source and a light detector in receiving relationship to the light source, the light source and light detector providing an optical path, comprising:

a transparent test document supporting a plurality of stripes of predetermined optical density, the stripes being arranged in descending optical density about a stripe of maximum density, a transporter for conveying the test document into communication with the optical path of each sensor, and circuitry responsive to the stripes of predetermined optical density to provide a timing pulse of response of each sensor to the test document, the timing pulse being a digital step pulse identifying the range of optical sensitivity each sensor, the step pulse representing a given set of stripes providing a detector signal exceeding a threshold value.

11. An apparatus according to claim 10 wherein the width of the digital step pulse is an indicator of the speed of the test document.

12. An apparatus according to claim 10 including a logic device responsive to the timing pulse of a given sensor for automatically adjusting said sensor to detect a predetermined number of stripes.

13. An apparatus according to claim 12 wherein the logic device adjusts the power to the sensor.

14. An apparatus according to claim 12 wherein the logic device adjusts the threshold value.

15. An apparatus for diagnosing the condition of a copy substrate sensor, the sensor including a light source and a light detector providing an optical path, comprising:

a test document including a plurality of sections of predetermined optical density, a transporter for conveying the test document into communication with the optical path of each sensor, circuitry responsive to the sections of predetermined optical density to provide a timing pulse representative of the optical sensitivity of the sensor, and a logic device responsive to the timing pulse to determine the inoperability of said sensor.

16. An apparatus according to claim 15 wherein the logic device is responsive to the timing pulse to adjust power to the sensor.

17. An apparatus according to claim 15 wherein the logic device determines that the timing pulse exceeds a threshold value.

18. An apparatus according to claim 17 wherein the logic device is responsive to the timing pulse to adjust the threshold value.

19. A portable diagnostics device for interconnection to a machine for diagnosing copy substrate sensors within the machine, the machine capable of transporting a test document past the sensors, the test document including a plurality of stripes of given density, comprising:

an interface for electrically connecting the portable diagnostic device to the machine, circuitry responsive to the stripes of predetermined optical density to provide a timing pulse representative of the optical sensitivity of each sensor, a logic device responsive to the timing pulse to determine the operability of each sensor, and memory to store operability data related to each sensor.

20. The portable diagnostic device of claim 19 wherein the timing pulse is a digital step pulse identifying the range of optical sensitivity each sensor.

21. The portable diagnostic device of claim 20 wherein the step pulse represents a given set of said plurality of stripes, said set providing a sensor signal exceeding a given threshold value.

22. The portable diagnostic device of claim 19 wherein the logic device is responsive to the timing pulse to adjust the sensor.

\* \* \* \* \*